United States Patent

Yamauchi et al.

[11] Patent Number: 5,876,578
[45] Date of Patent: Mar. 2, 1999

[54] GAS SENSOR

[75] Inventors: Shiro Yamauchi; Tadao Minagawa; Satoshi Higashinakagawa; Hiroshi Maekawa; Mitsuhito Kamei; Chieko Nishida, all of Tokyo; Shigemitsu Okabe; Takahiro Ohno, both of Kanagawa, all of Japan

[73] Assignee: Mitsubishi Denki Kabushiki Kaisha, Tokyo, Japan

[21] Appl. No.: 889,595

[22] Filed: Jul. 8, 1997

[30] Foreign Application Priority Data

Jul. 12, 1996 [JP] Japan .................................. 8-183219

[51] Int. Cl.⁶ .................................................. G01N 27/407
[52] U.S. Cl. ........................ 204/424; 204/425; 204/426; 205/778.5; 205/779.5
[58] Field of Search .................... 204/421–429; 205/778.5, 779.5, 780, 783.5

[56] References Cited

U.S. PATENT DOCUMENTS

| | | | |
|---|---|---|---|
| 3,431,182 | 3/1969 | Frant | 204/419 |
| 3,719,564 | 3/1973 | Lilly et al. | 205/783.5 |
| 3,727,058 | 4/1973 | Schrey | 204/426 |
| 3,764,269 | 10/1973 | Oldham et al. | 204/421 |
| 3,821,090 | 6/1974 | Topol et al. | 204/426 |
| 4,306,957 | 12/1981 | Ishitani et al. | 204/426 |
| 4,428,800 | 1/1984 | Tarcy | 205/779.5 |
| 4,707,224 | 11/1987 | Shabrang | 204/421 |
| 4,718,991 | 1/1988 | Yamazoe et al. | 204/421 |
| 4,797,194 | 1/1989 | Mase et al. | 204/426 |
| 4,828,673 | 5/1989 | Maeda | 204/421 |
| 4,900,405 | 2/1990 | Otagawa et al. | 204/412 |
| 5,080,775 | 1/1992 | Yamauchi et al. | 204/424 |
| 5,128,020 | 7/1992 | Yamauchi et al. | 204/424 |
| 5,556,534 | 9/1996 | Alcock et al. | 205/783.5 |

FOREIGN PATENT DOCUMENTS

| | | |
|---|---|---|
| 62-207952 | 9/1987 | Japan . |
| 64-75957 | 3/1989 | Japan . |
| 1-131034 | 5/1989 | Japan . |

Primary Examiner—T. Tung
Attorney, Agent, or Firm—Burns, Doane, Swecker & Mathis, LLP

[57] ABSTRACT

A gas sensor which can be used for measuring a low concentration repeatedly, which has a quick response and which can be used for a long time with high stability is provided. The gas sensor comprises a solid electrolyte, a detecting electrode provided in contact with one of the surfaces of the solid electrolyte and exposed to a gas to be detected, a counter electrode, provided in contact with the other surface of the solid electrolyte, and lead wires to place an electric voltage across both electrodes or to take out electric signals, wherein an inactive substance which is hard to form a reaction product with the gas to be detected is used as a material to constitute both electrodes.

17 Claims, 9 Drawing Sheets

GAS SENSOR

BACKGROUND OF THE INVENTION

1. Field of the Invention

The present invention relates to a gas sensor for detecting a trace amount of a gas component, and in particular it is related to a gas sensor which detects a decomposed gas resulting from decomposition of $SF_6$ due to a discharge which has taken place inside of a gas-insulated electrical apparatus.

2. Description of the Related Art

FIG. 13 shows an exemplary conventional gas sensor, which is described in Japanese Patent Laid-Open No. 62-207952. In this figure, a detecting electrode 1 is made of a mixture of a metal halide and a metal ion conductive solid electrolyte, and is so structured that the gas to be detected is allowed to be contacted with it. A solid electrolyte 2 is a solid conductor of metal ions. In this illustrative example, the metal is Ag, the metal ion is $Ag^+$, and the solid electrolyte is a solid conductor of $Ag^+$ ions. A counter electrode 3 is made of a mixture of a metal halide, a metal and a metal ion conductive solid electrolyte. Lead wires 5-1 and 5-2 attached to each electrode 1 and 3, are connected to a voltmeter having a high internal resistance.

The operation of the gas sensor structured as above and applied to a gas-insulated electrical apparatus is explained below. In the above-mentioned publication, the gas component resulting from decomposition of $SF_6$ by discharge is explained to be $F_2$ but generally it is considered to be HF. Assuming that the gas produced by the discharge is HF, the following reaction takes place on the detecting electrode 1:

2HF (on the detecting electrode)+2 $Ag^+$ (on the solid electrolyte)+$2e^-$ (on the metal)→$2AgF+H_2$ On the other hand, the following reaction takes place on the counter electrode 3.

2AgF (on the counter electrode)→$F_2$ (on the counter electrode)+$2Ag^+$ (on the solid electrolyte)+$2e^-$ (on the metal).

The composition is so set that the activity (partial pressure) of $F_2$ generated on the counter electrode 3 becomes constant. The electromotive force between the detecting electrode 1 and the counter electrode 3 is represented by the following equation according to the Nernst equation.

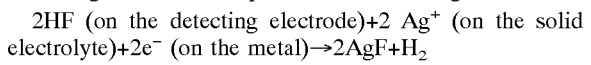

wherein, E: the electromotive force

A, B: constants $P_{HF}$: the partial pressure of HF on the detecting electrode side.

Accordingly, if the relation between the partial pressure of HF ($P_{HF}$) and the electromotive force (E) is obtained previously, the partial pressure of HF, that means that the concentration of the decomposed gas generated by discharge, can be obtained by measuring E at the time of the measurement.

One of the problems of the conventional gas sensor having the above-mentioned features is that it cannot be used repeatedly since the detecting electrode 1 material reacts with the gas to be detected and forms a reaction product. That means that, when the hydrogen fluoride (HF) which is the gas resulting from the decomposition by discharge is detected with the detecting electrode 1 which is made of silver (Ag), as the resulting silver fluoride (AgF) is a stable compound, even when the concentration of the gas to be detected (HF) is lowered, the output voltage is not decreased correspondingly, but keeps the signal level of the highest gas concentration. Therefore it has been impossible to carry out the measurement which attributed to the decrease of the concentration.

Also, since the output is generated as a result of the natural reaction between the gas to be detected (HF) and the electrode active substance ($Ag^+$ ion) on the electrode, the time required for the reaction is long. For instance, sometimes the response time becomes some hours or more. Therefore, the detection can not be done quickly, and this has been another problem of the conventional gas sensor.

SUMMARY OF THE INVENTION

The present invention has been achieved in order to solve the above-mentioned problems, and its object is to provide a gas sensor which can be repeatedly used for measuring even a low concentration, which has a quick response, and which can be used for a long time with high stability.

A gas sensor according to the present invention comprises a solid electrolyte, a detecting electrode provided in contact with one of the surfaces of the above-mentioned solid electrolyte and exposed to a gas to be detected, a counter electrode provided in contact with the other surface of the above-mentioned solid electrolyte, and lead wires to place an electric voltage across the above-mentioned electrodes or to conduct electric signals from the electrodes, wherein an inactive substance which is hard to form a reaction product with the gas to be detected is used as a material to constitute both the above-mentioned electrodes.

In a gas sensor according to the present invention, Au or carbon may be used as the material which is included in both the above-mentioned electrodes.

In a gas sensor according to the present invention, both the above-mentioned electrodes may be constituted by a thin Au or carbon film, and the thickness of the thin film layer may be between 20 and 30 nm.

In a gas sensor according to the present invention, both the above-mentioned electrodes may be constituted by a mixed layer of finely divided particles of Au or carbon, and finely divided particles of a solid electrolyte.

In a gas sensor according to the present invention, the solid electrolyte may be a fluorine ion conductive substance.

In a gas sensor according to the present invention, the solid electrolyte may be a $LaF_3$ single crystal to which europium or barium is added.

In a gas sensor according to the present invention, the detecting electrode may be divided into a plurality of parts.

In a gas sensor according to the present invention, means to remove a reaction product generated on the electrode may be provided in the vicinity of the electrode.

In a gas sensor according to the present invention, hydrogen gas removing means or fluorine gas removing means may be provided as the reaction product removing means.

In a gas sensor according to the present invention, an electrochemical cell comprising a hydrogen ion conductive solid electrolyte upon the both surfaces of which are secured electrodes, or a hydrogen occluding alloy may be used as the hydrogen gas removing means.

In a gas sensor according to the present invention, an electrochemical cell comprising a fluorine ion conductive solid electrolyte upon the both surfaces of which are secured electrodes, or an adsorbing agent may be used as the fluorine gas removing means.

DESCRIPTION OF THE PREFERRED EMBODIMENTS

Figure 1:
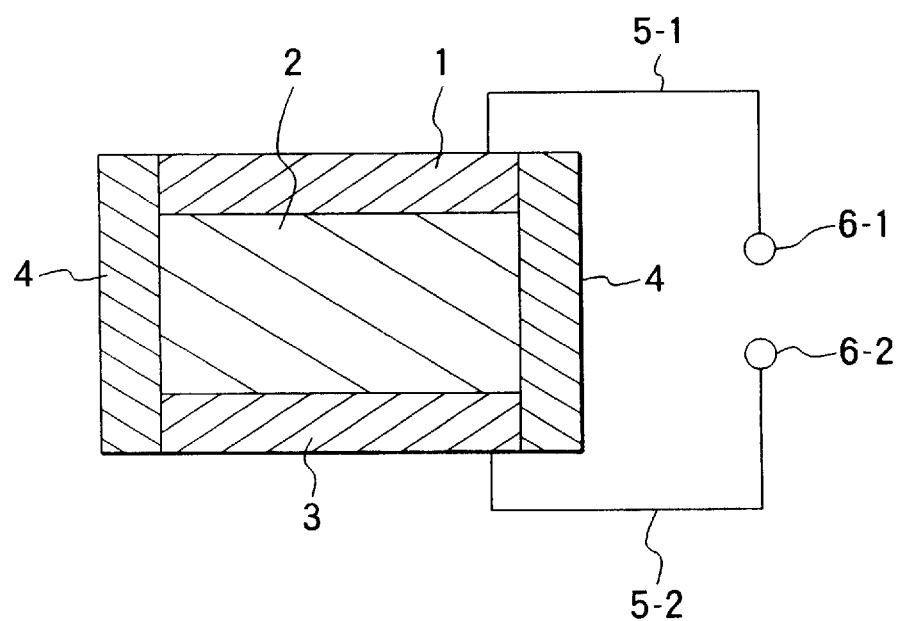
FIG. 1 is a cross-sectional view illustrating the composition of the gas sensor according to Embodiment 1 of the present invention.

Embodiment 1:

FIG. 1 illustrates a gas sensor according to Embodiment 1 of the present invention, having a detecting electrode 1, a solid electrolyte 2, a counter electrode 3, an insulator 4, lead wires 5-1 and 5-2, and terminals 6-1 and 6-2. The solid electrolyte 2 is a substance which is a conductor of fluorine ions. For example, it is a single crystal of $LaF_3$ to which europium is added in an amount of 0.3 mol %, having a thickness of 0.2 mm. The addition of europium lowers the electric resistance of the $LaF_3$ single crystal and shortens the time constant, or the time required for the output of the gas sensor to reach the steady state. The merits of the single crystal include the uniformity of the material and easy processing. Both the detecting electrode 1 and the counter electrode 3 are made of gold thin films and formed by sputtering on both surfaces of the solid electrolyte. The thickness of the sputtered thin film is 25 nm and this figure is an average of 20 nm and 30 nm, since when it is thinner than 20 nm the electrode resistance becomes too high, and when it is thicker than 30 nm, the permeation of the gas to be detected becomes inferior. DC 2.5 V is applied (though not shown in the figure) to terminals 6-1 and 6-2 so that the side of the detecting electrode 1 becomes the negative electrode (cathode) and the side of the counter electrode 3 becomes the positive electrode (anode). The measurement of the electric current flowing at this time was done by Source Measure Unit 238 Type having an electric voltage applying function and an electric current measuring function, produced by KEITHLEY Co.

The gas to be detected is a gas resulting from decomposition of $SF_6$ caused by discharge in a gas-insulated electric apparatus. When $SF_6$ gas is exposed to an electric arc or corona discharge, HF, $SF_4$, $SOF_2$, and $SO_2$ are generated by the discharge decomposition according to the following reactions. Here, the explanation is based on the case in which copper is used as a conductor of generating the electric arc and corona discharge.

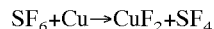
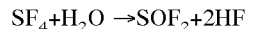
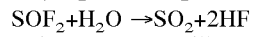

Using HF as an illustrative example, the case of HF reaching the detecting electrode 1 will be explained. The following reaction takes place on the detecting electrode 1;

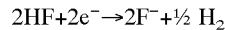

and the resulting $F^-$ migrates through the solid electrolyte 2 towards the counter electrode 3, and there the following reaction takes place.

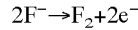

Figure 2:
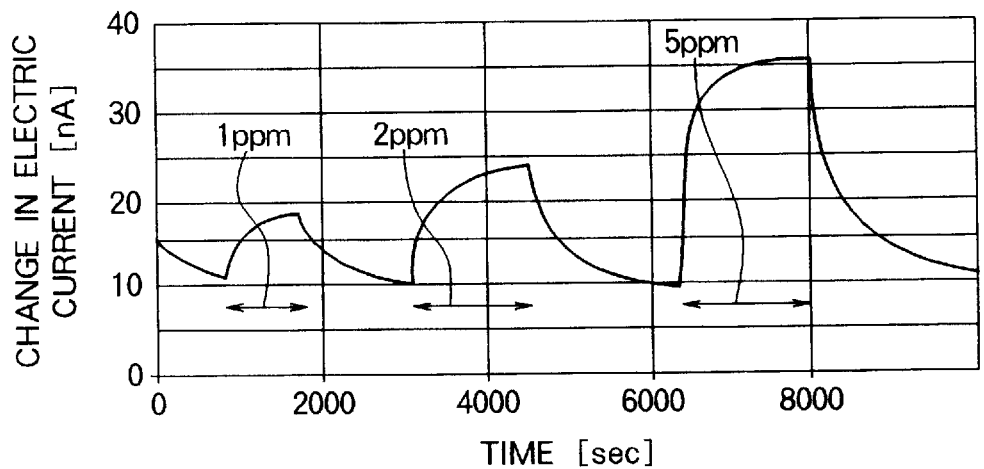
FIG. 2 is a graph showing the characteristics of a gas sensor according to the Embodiment 1.
Figure 3:
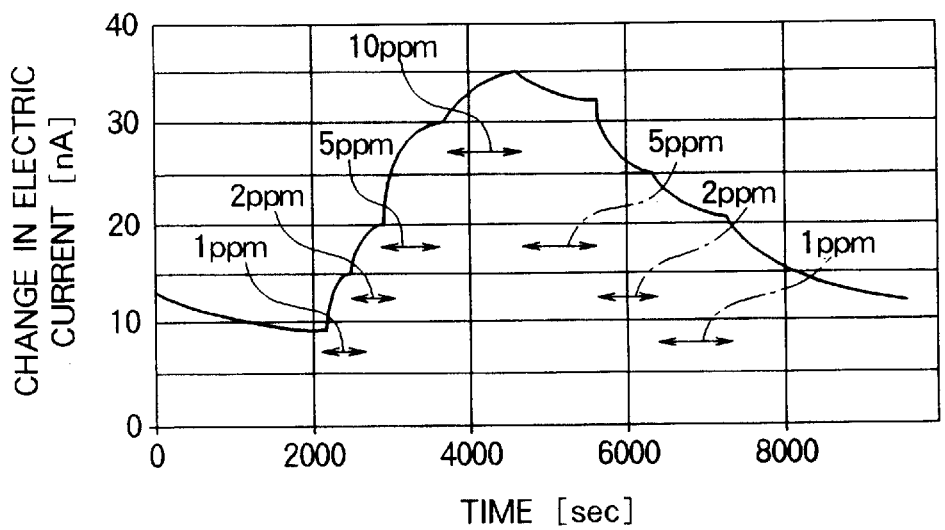
FIG. 3 is a graph showing the characteristics of a gas sensor according to the Embodiment 1.
Figure 4:
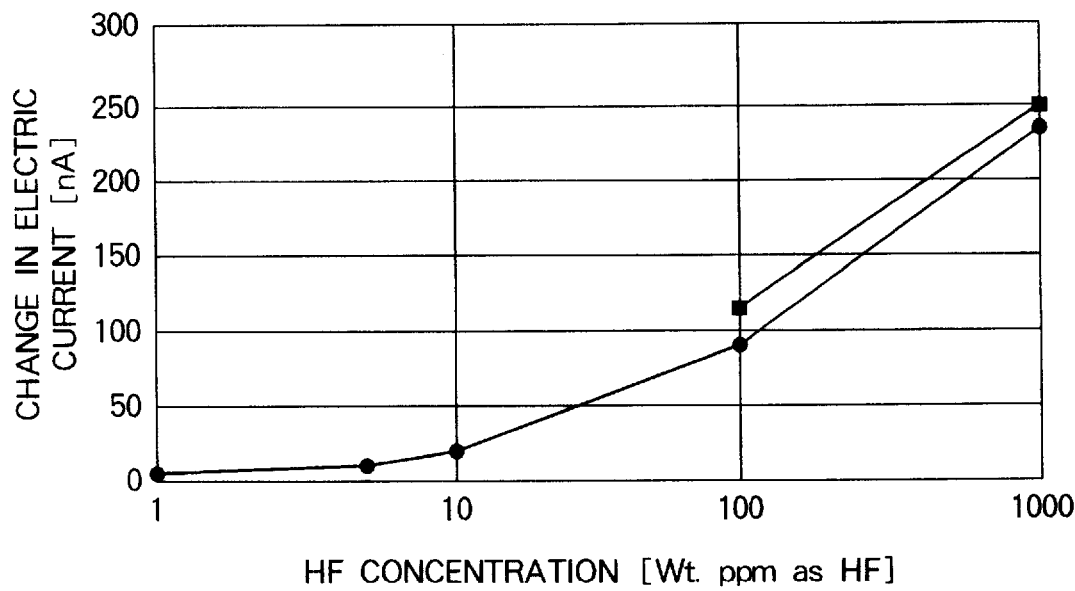
FIG. 4 is a graph showing the characteristics of a gas sensor according to the Embodiment 1.

The response characteristics of this gas sensor to HF gas are shown in FIG. 2 and FIG. 3. In a range of HF concentrations from 1 ppm to 5 ppm, the gas sensor's response was found to be satisfactory. The relation between the gas concentrations and the change in the output electric current when the concentration range is extended to a high concentration side (up to 1000 ppm) is shown in FIG. 4. The gas sensor was confirmed to respond sufficiently to the gas concentrations up to 1000 ppm.

Embodiment 2:

Similar results were obtained when carbon thin film electrodes (thickness of 25 nm) were used instead of Au thin film electrodes. The return to the base line after the gas to be detected was gone was quicker than that obtained with the Au thin film electrodes and the electric current value of the base line was able to be maintained at a low level. Thus the carbon thin film electrodes showed that they had as good characteristics as those of the Au thin film electrodes.

The reason why the Au electrode and the carbon electrode allow measurement of a low HF concentration repeatedly with a relatively quick response is that HF hardly forms a reaction product with the Au electrode or the carbon electrode.

Figure 5:
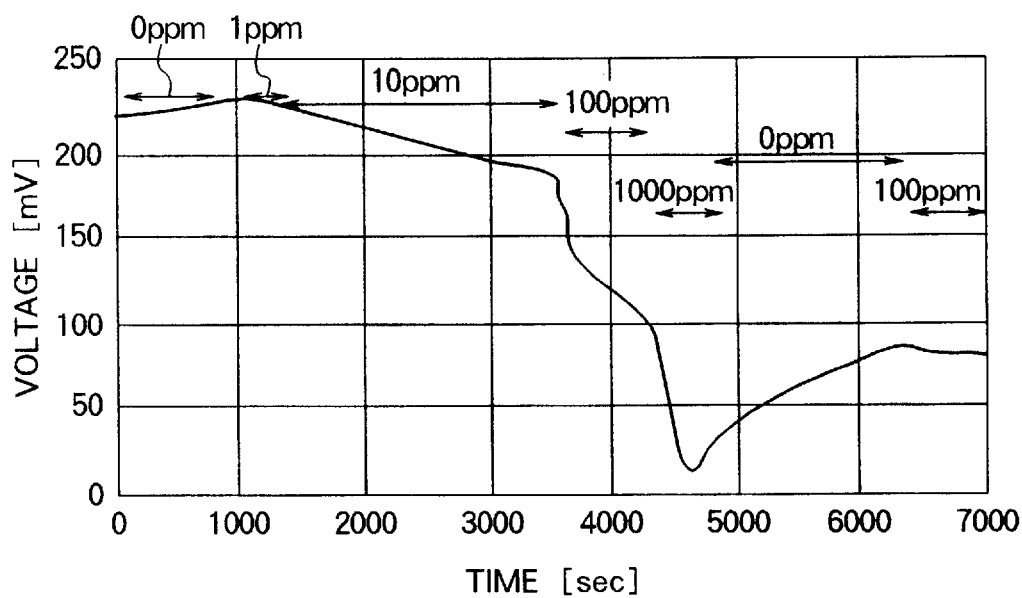
FIG. 5 is a graph showing the characteristics of a gas sensor according to Embodiment 3 of the present invention.
Figure 6:
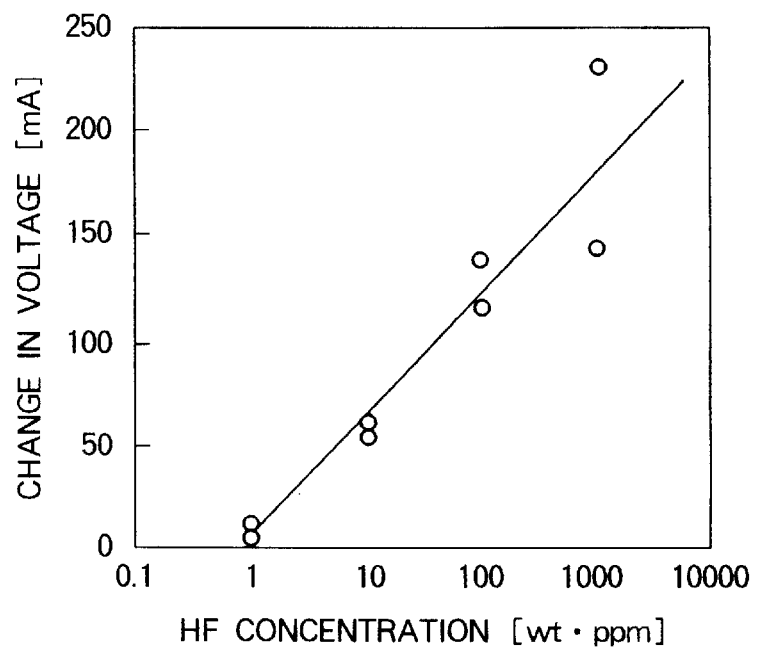
FIG. 6 is a graph showing the characteristics of a gas sensor according to the Embodiment 3.

Embodiment 3:

In the above-mentioned Embodiment 1, the apparatus for applying an electric voltage and for measuring an electric current was connected between the terminals 6-1 and 6-2. Now, an exemplary gas sensor of an electric voltage output type is shown as follows. A voltmeter, Electrometer 6512 type, produced by KEITHLEY Co., having an internal impedance of at least $10^{14}\Omega$ was connected between the terminals 6-1 and 6-2 in the FIG. 1. The response characteristics to the gas to be detected in this case was shown in FIG. 5. FIG. 6 illustrates the relation between the gas concentration and the output voltage. it was confirmed that the gas sensor responded well according to the gas concentrations up to 1000 ppm.

Figure 7:
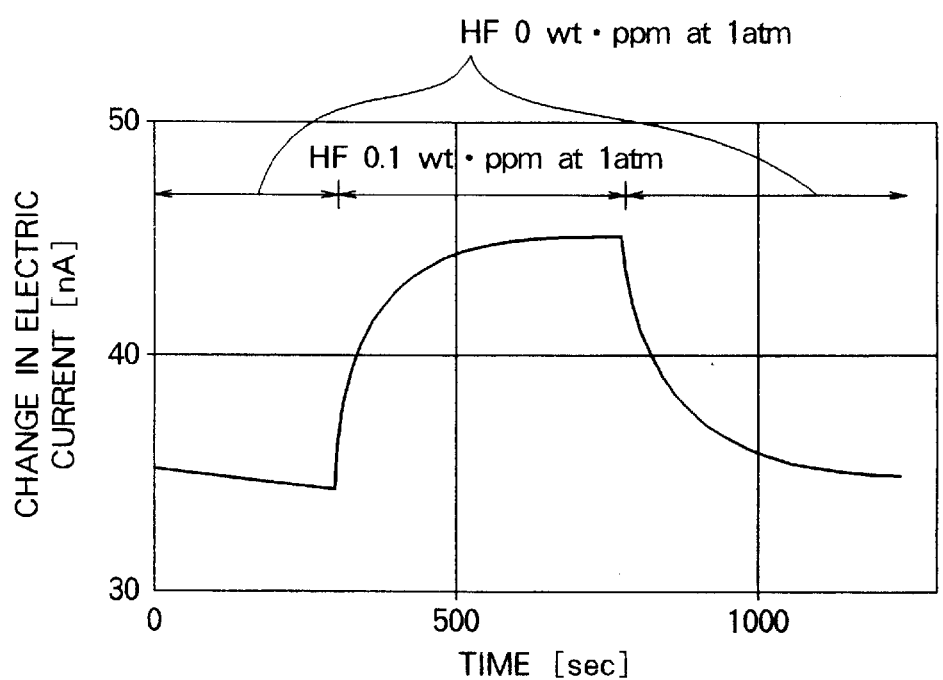
FIG. 7 is a graph showing the characteristics of a gas sensor according to Embodiment 4 of the present invention.

Embodiment 4:

The electrode in this Embodiment is made of a mixed layer of finely divided Au particles and finely divided solid electrolyte particles. The solid electrolyte is a single crystal of $LaF_3$ to which barium is added in an amount of 0.3 mol %, and the thickness is 0.2 mm. As is the case with the above-mentioned addition of europium, the addition of the barium lowers the electric resistance of the solid electrolyte and shortens the time constant or the time required for the output of the gas sensor to reach the steady state. Similar to the Embodiment 1, DC 2.5 V was applied to the terminals 6-1 and 6-2 in FIG. 1, so that the side of the detecting electrode 1 became the negative electrode (cathode) and the side of the counter electrode became the positive electrode (anode) and the electric current flowing through the resulting circuit was measured. The results are shown in FIG. 7. Sufficient response to the HF of 0.1 wt. ppm (at 1 atm) in $SF_6$ was confirmed. This sensitivity corresponds to 0.02 wt. ppm, i.e. 20 wt. ppb under normal $SF_6$ gas pressure (5 atm) of a gas-insulated electric apparatus. This is because the material related to the electrode reaction is pulverized, the reaction spots are increased to enhance the sensitivity.

Instead of the finely divided particles of Au, finely divided particles of carbon were used for a mixed layer and the resulting mixed layer electrode showed results similar to those mentioned above.

Figure 8:
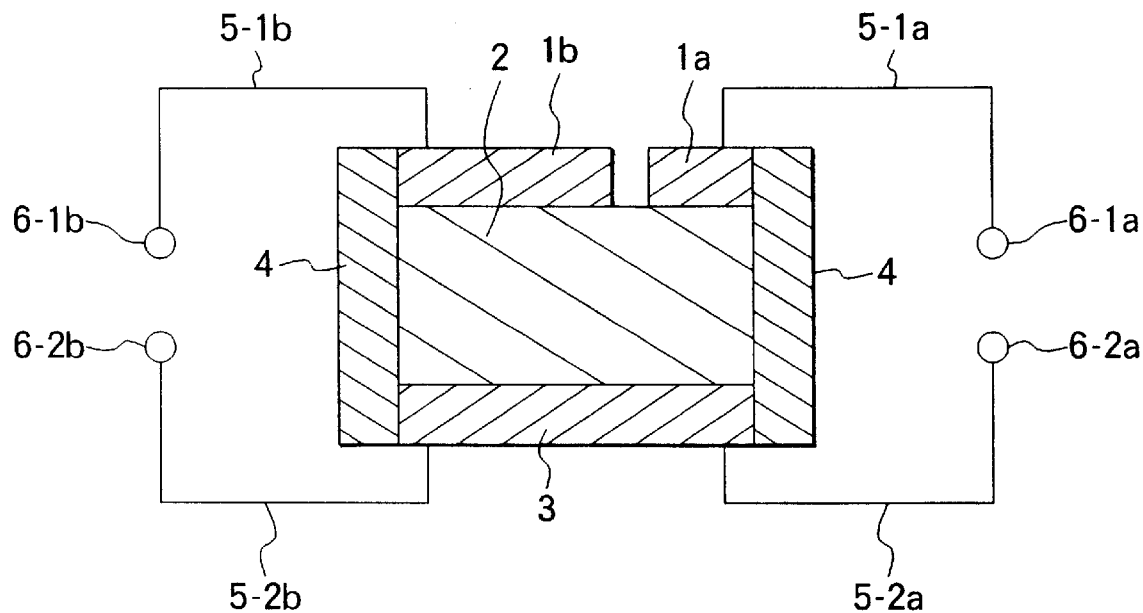
FIG. 8 is a cross-sectional view illustrating the composition of the gas sensor according to Embodiment 5 of the present invention.
Figure 9:
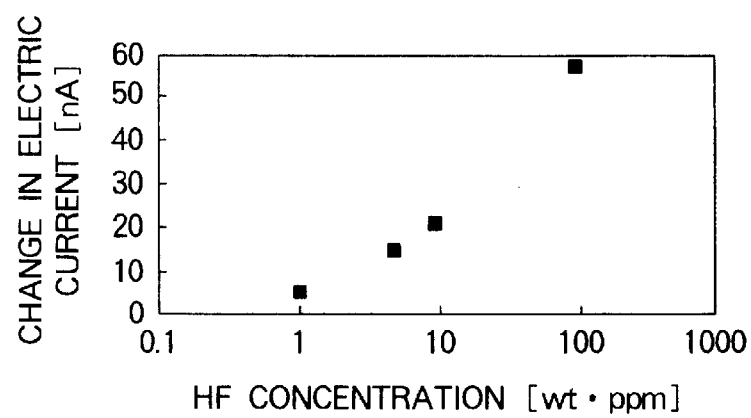
FIG. 9 is a graph showing the characteristics of a gas sensor according to the Embodiment 5.
Figure 10:
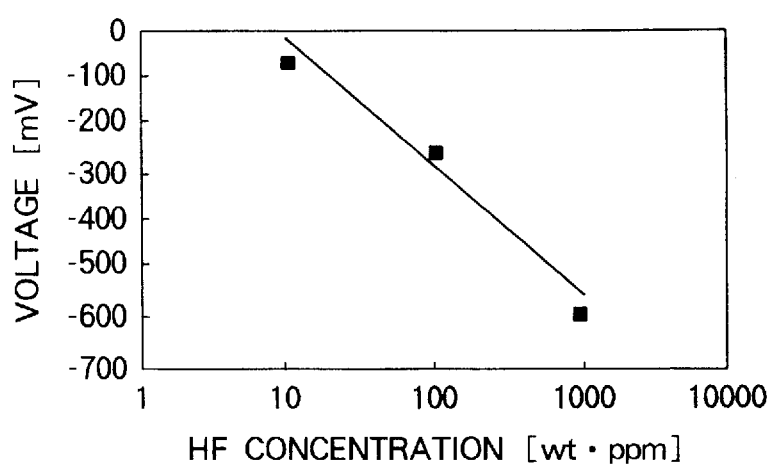
FIG. 10 is a graph showing the characteristics of a gas sensor according to the Embodiment 5.

Embodiment 5:

FIG. 8 illustrates the composition of a gas sensor in which a plurality of electrodes for detecting the gas to be detected are so provided on a solid electrolyte 2 that they are not in contact with each other. In the FIG. 8, first detecting electrode 1a and second detecting electrode 1b are made of Au sputtered thin films. The thickness of the sputtered thin film was set as 25 nm as was the case with the Embodiment 1. A solid electrolyte 2 was a single crystal of $LaF_3$ to which europium was added in an amount of 0.3 mol %, and the thickness was 0.2 mm. A counter electrode 3 was a single electrode which was not divided and the material and the thickness were the same as those of the detecting electrodes 1-a and 1-b. 2.5 V of DC electric voltage (not shown in the figure) was applied to the terminals 6-1b and 6-2b, so that the side of the detecting electrode became the negative electrode (cathode) and the side of the counter electrode became the positive electrode (anode) and the electric current of this system was measured. A voltmeter (not shown in the figure) was connected between the terminals 6-1a and 6-2a. The detection capacity of the present gas sensor is shown in FIG. 9 (electric current output) and FIG. 10 (electric voltage output). The outputs without any saturation were obtained in both the electric current and the electric voltage system to HF concentrations from 1 to 1000 ppm.

Figure 11:
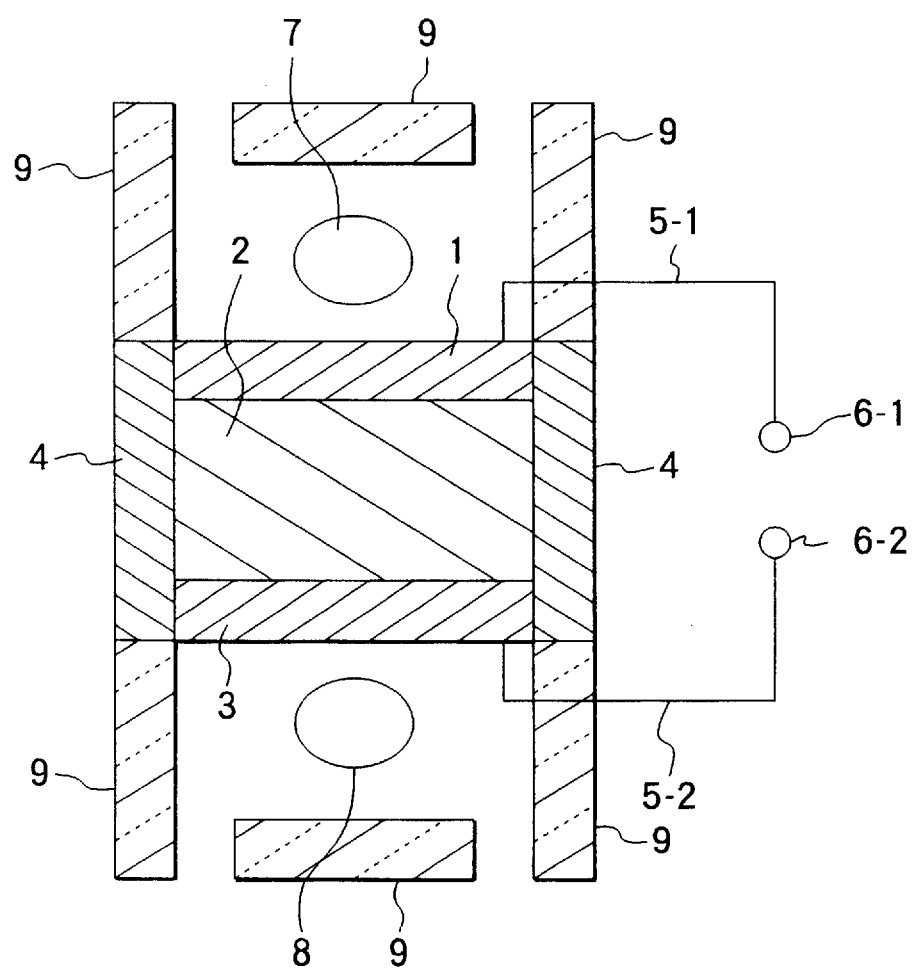
FIG. 11 is a cross-sectional view illustrating the composition of the gas sensor according to Embodiment 6 of the present invention.

Embodiment 6:

An exemplary gas sensor having means to remove the reaction products produced on the electrodes is shown in FIG. 11. In this figure, the reaction product removing means 7 (on the detecting electrode side), the reaction product removing means 8 (on the counter electrode side) and cover 9 are illustrated.

In the case of a gas obtained from decomposition of $SF_6$, using HF as an illustrative example, the following reaction takes place on the detecting electrode.

$2HF + 2e^- \rightarrow H_2 + 2F^-$

On the other hand, the following reaction takes place on the counter electrode.

$2F^- \rightarrow F_2 + 2e^-$

Accordingly, $H_2$ is generated on the detecting electrode, and $F_2$ is generated on the counter electrode. $H_2$ and $F_2$ being present in the vicinity of the electrodes leads to errors in the measurement of the gas sensor the original purpose of which is to measure the gas resulting from the decomposition of $SF_6$ by discharge in the gas-insulated electric apparatus. Therefore those gasses are desired to be removed. In this embodiment, a hydrogen occluding alloy is used to remove the $H_2$ generated on the detecting electrode, and a synthesized zeolite adsorbent is used to remove $F_2$ generated on the counter electrode.

Figure 12:
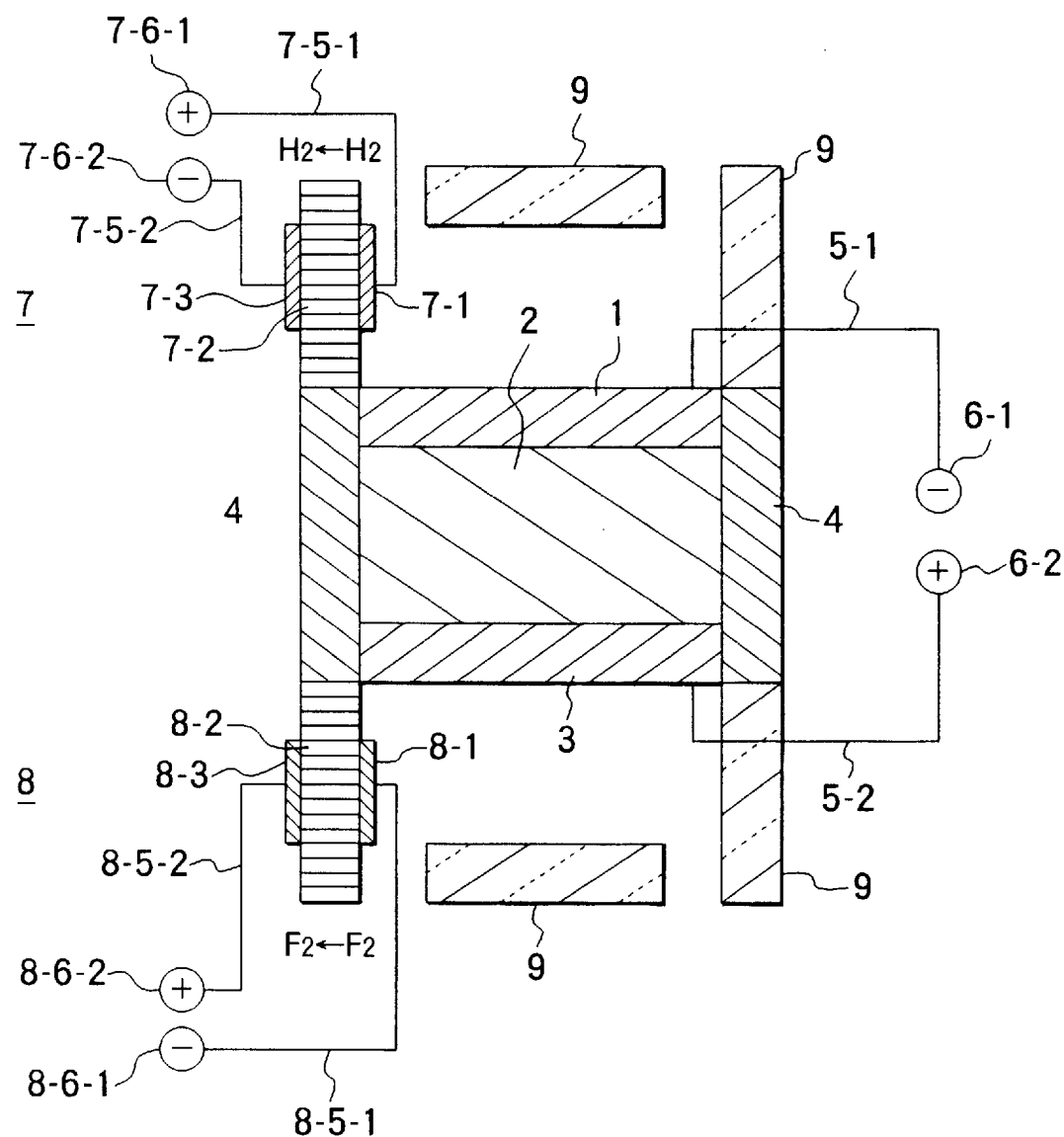
FIG. 12 is a cross-sectional view illustrating the composition of the gas sensor according to Embodiment 7 of the present invention.
Figure 13:
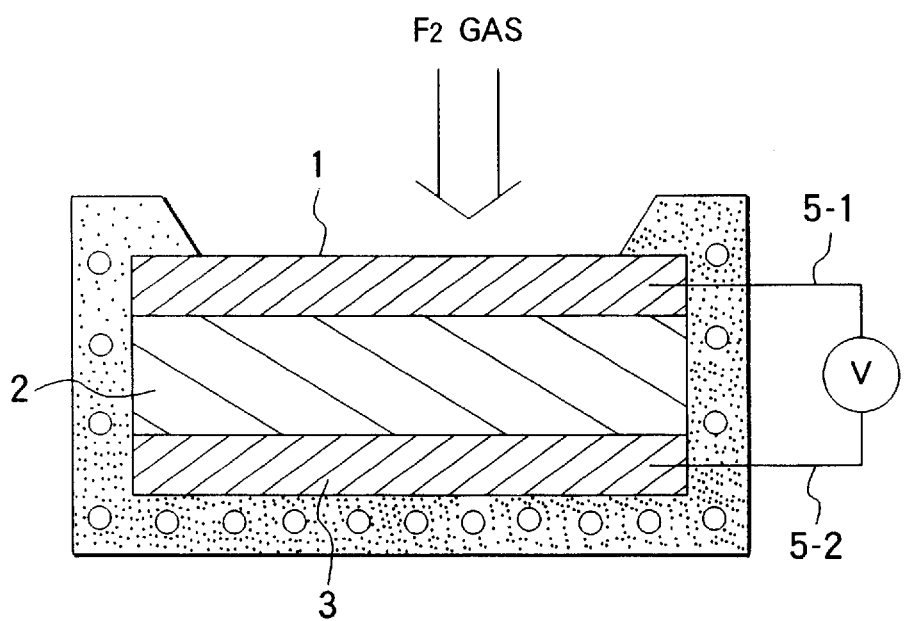
FIG. 13 is a cross-sectional view illustrating the composition of the conventional gas sensor.

Embodiment 7:

FIG. 12 illustrates an example of a gas sensor in which $H_2$ and $F_2$ generated on the detecting electrode and counter electrode are removed by "reaction product removing means using an electrochemical cell". The reaction product removing means on the detecting electrode side and that on the counter electrode side are represented by numerals 7 and 8 respectively.

Referring now to FIG. 12, the removal of $H_2$ will be explained more specifically. The reaction product removing means 7 is an electrochemical cell comprising a separator 7-2 made of a hydrogen ion conductive solid electrolyte, and porous metal (Pt) thin film electrodes 7-1 and 7-3 secured on both surfaces thereof. As the solid electrolyte, uranyl phosphate hydrate ($HUO_2PO_4.4H_2O$) is used. 7-5-1 and 7-5-2 represent lead wires, and 7-6-1 and 7-6-2 represent terminals. DC voltage is so applied between these electrodes that the side of the sensor becomes the positive electrode and the side of the atmosphere becomes the negative electrode, and the following reactions take place;

On the sensor side: $H_2 \rightarrow 2H^+ + 2e^-$

On the atmosphere side: $2H^+ + 2e^- \rightarrow H_2$ $H_2$ on the sensor side is first ionized and enters the solid electrolyte then migrates towards the electrode on the atmosphere side, then it is gasified and released into air. In this way, the hydrogen gas generated on the detecting electrode 1 is removed from the system. One of the advantages is that the electrochemical cell can be operated semipermanently when a power source is connected.

Then, the removal of $F_2$ will be explained more specifically with reference to FIG. 12. The reaction product removing means 8 is an electrochemical cell comprising a separator 8-2 made of a fluorine ion conductive solid electrolyte and porous metal (Pt) thin film electrodes 8-1 and 8-3, secured on the both surfaces thereof. As the solid electrolyte, a single crystal of $LaF_3$ to which europium is added in an amount of 0.3 mol % is used. 8-5-1 and 8-5-2 represent lead wires and 8-6-1, 8-6-2 represent terminals. When the DC voltage is applied between the electrodes so that the side of the sensor becomes the negative electrode and the side of the atmosphere becomes the positive electrode, the following reactions take place;

On the sensor side: $F_2 + 2e^- \rightarrow 2F^-$

On the atmosphere side: $2F^- \rightarrow F_2 + 2e^-$ $F_2$ on the sensor side is first ionized and enters the solid electrolyte, migrates towards the electrode on the atmosphere side, then it is gasified and released into air. In this way, fluorine gas generated on the counter electrode 3 is removed from the system. One of the advantages is that the electrochemical cell can be operated semipermanently when a power source is connected.

By the way, in the Embodiments shown above, a pair of the same kind of electrode materials, such as Au thin films, is used for both the detecting electrode 1 and the counter electrode 3. It is needless to say but a pair of different kinds of electrode materials, such as an Au thin film and a carbon thin film, can also be used.

The present invention constructed as above has the following advantages.

As the gas sensor according to the present invention has a solid electrolyte, a detecting electrode, a counter electrode and lead wires, and an inactive substance which is hard to form a reaction product with the gas to be detected is used as a material to constitute these electrodes, a low concentration of the gas to be detected can be measured repeatedly and a quick response can be obtained.

Where Au or carbon is used as a material to constitute the electrode, the electrode scarcely forms a reaction product with the gas to be detected, and the low concentration of the gas to be detected can be measured repeatedly and a quick response can be obtained.

Where the electrode comprises a thin Au or carbon film having a thickness of 20–30 nm, a good electrode can be provided whose electric resistance is not too high, which has a satisfactory permeability of the gas to be detected.

Where the electrode comprises a mixed layer of finely divided particles of Au or carbon and finely divided particles of a solid electrolyte, a gas sensor of high sensitivity can be provided.

Where the solid electrolyte is a fluorine ion conductive substance, the gas sensor can measure the concentration of a gas, including HF, which is produced by decomposition of $SF_6$ by discharge.

Where the solid electrolyte comprises a $LaF_3$ single crystal to which europium or barium is added, the electric resistance of the solid electrolyte is low and the time constant, or the time for the output of the gas sensor to reach the steady state can be shortened.

Where the detecting electrode is divided in a plurality of parts and so provided that they are not in contact with each other, a plurality of data can be simultaneously obtained with only single gas sensor.

Where means to remove the reaction product generated on the electrode is provided in the vicinity of the electrode, accurate data which are not influenced by the reaction product can be obtained.

Where hydrogen gas removing means or fluorine gas removing means is provided as means to remove the reaction product, accurate data which are not influenced by the remaining hydrogen gas or remaining fluorine gas can be obtained.

Where an electrochemical cell comprising a hydrogen ion conductive solid electrolyte and electrodes secured on the both surfaces thereof, or a hydrogen occluding alloy is used as hydrogen gas removing means, accurate data which are not influenced by the remaining hydrogen gas can be obtained.

Where an electrochemical cell comprising a fluorine ion conductive solid electrolyte and electrodes secured on the both surfaces thereof, or an adsorbing agent is used as fluorine gas removing means, accurate data which are not influenced by remaining fluorine gas can be obtained.

While the invention has been described in detail and with reference to specific embodiments thereof, it will be apparent to one of ordinary skill in the art that various changes and modifications can be made therein without departing from the spirit and scope thereof.

What is claimed is:

1. A gas sensor comprising:

a solid electrolyte;

a detecting electrode provided in contact with one of the surfaces of said solid electrolyte and exposed to a gas to be detected;

a counter electrode provided in contact with the other surface of said solid electrolyte;

lead wires to place an electric voltage across said electrodes or to take out electric signals;

wherein an inactive substance which is hard to form a reaction product with the gas to be detected is used as a material for both of said electrodes; and means for removing a reaction product generated on one of said electrodes, wherein said means for removing is provided in the vicinity of said one electrode.

2. The gas sensor according to claim 1, wherein Au or carbon is used as the material for the electrodes.

3. The gas sensor according to claim 2, wherein each electrode is comprised of a thin Au or carbon film, and the thickness of the thin film is between 20 and 30 nm.

4. The gas sensor according to claim 2, wherein the electrode is comprised of a mixed layer of finely divided particles of Au or carbon, and finely divided particles of a solid electrolyte.

5. The gas sensor according to claim 1, wherein the solid electrolyte comprises a fluorine ion conductive substance.

6. The gas sensor according to claim 5, wherein the solid electrolyte comprises a $LaF_3$ single crystal to which europium or barium is added.

7. The gas sensor according to claims 1, wherein said means for removing comprises one of: a hydrogen gas removing element and a fluorine gas removing element.

8. The gas sensor according to claim 7, wherein said hydrogen gas removing element comprises one of: an electrochemical cell comprising a hydrogen ion conductive solid electrolyte having electrodes disposed on both surfaces thereof, and a hydrogen occluding alloy.

9. The gas sensor according to claim 7, wherein said fluorine gas removing element comprises one of: an electrochemical cell comprising a fluorine ion conductive solid electrolyte having electrodes disposed on both surfaces thereof, and an adsorbing agent.

10. The gas sensor according to claim 1, wherein:

the gas to be detected includes HF;

the detecting electrode is comprised of one of: Au and carbon;

the counter electrode is comprised of one of: Au and carbon; and the solid electrolyte comprises a fluorine ion conductive substance.

11. The gas sensor according to claim 10, wherein the HF gas is detected in response to the following reactions at the detecting electrode and the counter electrode:

detecting electrode: $2HF + 2e^- \rightarrow 2F^- + \frac{1}{2}H_2$ counter electrode: $2F^- \rightarrow F_2 + 2e^-$.

12. The gas sensor according to claim 1, wherein said means for removing a reaction product generated on an electrode comprises first and second elements for removing first and second reaction products, wherein said first element is provided in the vicinity of said detecting electrode and said second element is provided in the vicinity of said counter electrode.

13. The gas sensor according to claim 12, wherein said first element comprises a hydrogen gas removing element and said second element comprises a fluorine gas removing element.

14. The gas sensor according to claim 13, wherein:

said hydrogen gas removing element comprises one of: an electrochemical cell comprising a hydrogen ion conductive solid electrolyte having electrodes disposed on both surfaces thereof, and a hydrogen occluding alloy.

15. The gas sensor according to claim 13, wherein:

said fluorine gas removing element comprises one of: an electrochemical cell comprising a fluorine ion conductive solid electrolyte having electrodes disposed on both surfaces thereof, and an adsorbing agent.

16. The gas sensor according to claim 13, wherein:

said hydrogen gas removing element comprises an electrochemical cell comprising a hydrogen ion conductive solid electrolyte having electrodes disposed on both surfaces thereof; and said fluorine gas removing element comprises an another electrochemical cell comprising a fluorine ion conductive solid electrolyte having electrodes disposed on both surfaces thereof.

17. The gas sensor according to claim 13, wherein:

said hydrogen gas removing element comprises a hydrogen occluding alloy, and said fluorine gas removing element comprises an adsorbing agent.

* * * * *